United States Patent [19]

Miyata et al.

[11] Patent Number: 4,892,681
[45] Date of Patent: Jan. 9, 1990

[54] NON-LINEAR OPTICAL ARTICLE

[75] Inventors: Seizo Miyata, Hoya; Toshiyuki Watanabe, Kurume; Yoshitaka Goto; Masaharu Nakayama, both of Ibaraki, all of Japan

[73] Assignee: Nippon Oil and Fats Co., Ltd., Tokyo, Japan

[21] Appl. No.: 102,193

[22] Filed: Sep. 29, 1987

[30] Foreign Application Priority Data

Sep. 30, 1986 [JP] Japan .................. 61-229612

[51] Int. Cl.$^4$ .................. G02B 5/00; G02B 6/14
[52] U.S. Cl. .................. 252/582; 252/600; 252/589; 350/353
[58] Field of Search .................. 568/306, 307, 334; 252/582, 600, 589

[56] References Cited

FOREIGN PATENT DOCUMENTS 2802440 7/1978 Fed. Rep. of Germany .

OTHER PUBLICATIONS

Lavrushin et al., Zh. Org. Khim. 1971, 7(7) 1459–1463.
Demus, "Flussige Kristalle in Tabellen", 1984, vol. II, p. 56.
Chemical Abstracts Service, Abstract #88:189450.
Chemical Abstracts Service, Abstract #88:95024.
Chemical Abstracts Service, Abstract #77:139520.
Chemical Abstracts Service, Abstract #75:129234.
Chemical Abstracts Service, Abstract #72:99703.
Chemical Abstracts Service, Abstract #72:99693.
ACS Symposium, 1983, Organic Materials, Tweig et al., Chp. 3, pp. 57–79.

Primary Examiner—Teddy S. Gron
Assistant Examiner—Richard Treanor
Attorney, Agent, or Firm—Jordan and Hamburg

[57] ABSTRACT

A non-linear optical article is constituted of a derivative of benzalacetophenone represented by the following general formula:

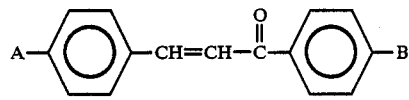

wherein A and B each represent the same or different atom or group and stand for a hydrogen atom, an alkoxy group having 1 to 4 carbon atoms, a chlorine atom, a bromine atom, an amino group or a dialkylamino group having 1 to 2 carbon atoms.

2 Claims, 1 Drawing Sheet

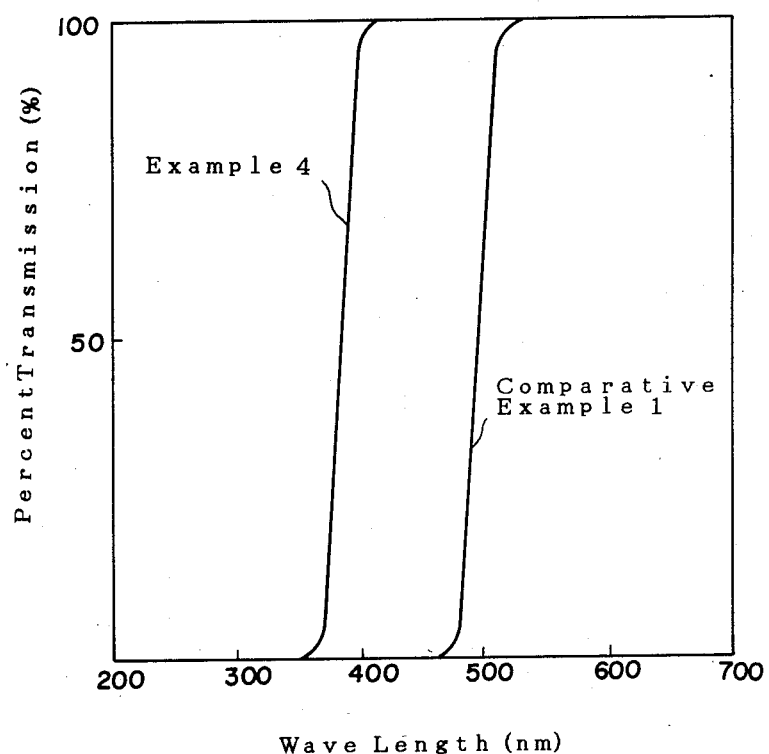
FIG.

NON-LINEAR OPTICAL ARTICLE

BACKGROUND OF THE INVENTION

1. Field of the Invention

The present invention relates to a non-linear optical article or material which exhibits non-linear response when used in an optical instrument or as an optical element or tool, and particularly to such an optical article or material constituted of a derivative of benzalacetophenone and a process for the preparation of such an optical article.

Non-linear optical materials include those in which non-linear response results due to induced polarization of electrons by the electric field created by the light incident to a material. In other words, the term "non-linear optical material" means materials for optical use, which exhibit the so-called non-linear optical effect. In general, such effect is due to the phenomenon which may be indicated by the second and higher order terms in the following equation of:

$$P = \chi^1 E + \chi^2 E \cdot E + \chi^3 E \cdot E \cdot E + \cdots + \chi^n E \cdot n;$$

wherein P is polarizability of a material, E is intensity of the electric field, and $\chi^n$ is non-linear sensitivity of the n-th power.

Particularly, when the phenomenon known as the second harmonic generation (SHG), which is obtainable by the utilization of the secondary effect, is intended to be applied to optical processing, the incident light is converted into two light waves both having frequencies corresponding to those of the second harmonic waves. This phenomenon may be conveniently utilized for a variety of optical processing including conversion of wave length, processing of signals and modulation of laser beams.

2. Related Art Statement

Crystals of inorganic compounds, such as KH$_2$PO$_4$ (KDP), LiNbO$_3$, NH$_4$H$_2$PO$_4$ (ADP), have hitherto been used as the non-linear optical materials. However, those known materials have several disadvantages, for instance, in that single crystals thereof having high optical purities are very expensive, that they often are deliquescent and, therefore absorb moisture from the atmosphere and thus cause problems in handling and that the non-linear sensitivities thereof do not reach satisfactory level.

On the other hand, since the utility of organic materials for such applications was reported in 1983 in a symposium of the American Chemical Society, there have been some reports which describe the use of crystals of organic compounds as non-linear optical materials. The compounds which have been already reported as having utility as non-linear optical materials include, for example, urea, aniline type compounds, and benzalacetophenones including nitro groups which are different from the compounds used in this invention. However, these known organic compounds do not exhibit satisfactory non-linear optical effects, or the compounds which exhibit relatively high level non-linear effects have cut off wavelengths that are significantly shifted onto the long wave length range to thus limit the wave length range of the light waves which can be processed therethrough.

OBJECTS AND SUMMARY OF THE INVENTION

Accordingly, a principal object of this invention is to provide a non-linear optical article which exhibits satisfactory non-linear optical response, and which is free from the aforementioned problems of the like articles constituted of the known non-linear optical materials and a process for the preparation of such an optical article.

These and other objects will be made clear by referring to the following description.

A non-linear optical article, provided in accordance with this invention, is constituted of a derivative of benzalacetophenone represented by the following general formula (I):

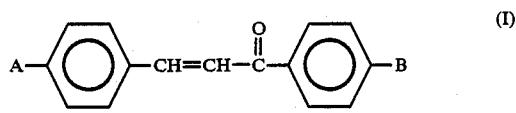

wherein A and B each represent the same or different atom or group and stand for a hydrogen atom, an alkoxy group having 1 to 4 carbon atoms, a chlorine atom, a bromine atom, an amino group or a dialkylamino group having 1 to 2 carbon atoms.

The article exhibiting a non-linear optical response, provided by the preferred embodiment of this invention has a percent transmission of 100% for visible light rays having wave lengths of not less than 400 nm.

According to the invention, there is also provided a process for the preparation of the aforementioned optical article represented by the general formula (I) comprising reacting, through dehydrating condensation reaction, a derivative of benzaldehyde represented by the following general formula (II):

wherein A is the same as defied above; with a derivative of acetophenone represented by the general formula (III):

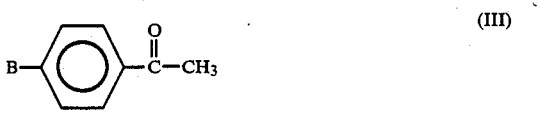

wherein B is the same as defied above; in the presence of a catalyst.

BRIEF DESCRIPTION OF THE DRAWING

The single FIGURE appended to this specification is a graph showing the light absorption spectra of Example 4 of this invention and a prior art non-linear optical material of Comparative Example 1.

DESCRIPTION OF THE INVENTION

The present invention will now be described in detail.

In the present invention, the non-linear optical article used for special optical applications is constituted of a derivative of benzalacetophenone represented by the following general formula (I):

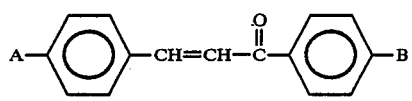 (I)

In the general formula (I), A and B each represent the same or different atom or group and stand for a hydrogen atom, an alkoxy group having 1 to 4 carbon atoms, a chlorine atom, a bromine atom, an amino group or a dialkylamino group having 1 to 2 carbon atoms.

The derivative of benzalacetophenone used in this invention may be prepared by reacting a derivative of benzaldehyde (II) and a derivative of acetophenone (III), the structural formulae (II) and (III) being set forth below, in the presence of a basic or acidic catalyst to effect a dehydrating condensation reaction.

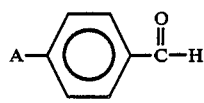 (II)

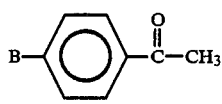 (III)

In the structural formulae (II) and (III), A and B each represent the same or different atom or group and stand for a hydrogen atom, an alkoxy group having 1 to 4 carbon atoms, a chlorine atom, a bromine atom, an amino group or a dialkylamino group having 1 to 2 carbon atoms.

Examples of the basic catalyst which may be used to accelerate the dehydrating condensation reaction are sodium hydroxide, potassium hydroxide, and a variety of quaternary ammonium salts. Examples of the acidic catalyst used for the same purpose are boron trifluoride, phosphorus oxychloride and boron trifuloride etherate.

The derivative of benzalacetophenone used in this invention may be prepared by reacting any one or more of the aforementioned derivatives of benzaldehyde (represented by Formula (II)) and any one or more of the derivatives of acetophenones (represented by the Formula (III)) in the presence of any one or more of the aforementioned catalysts, in an appropriate solvent, such as an alcohol (methanol, ethanol, etc.), at a temperature within the range of from 0° C. to 30° C. for 30 minutes to 10 hours. Reaction temperature of higher than 30° C. is not preferred since various side-reactions take place at such a higher temperature, and reaction temperature of lower than 0° C. is also not preferred from an economic standpoint since the time required for the completion of the reaction is prolonged significantly.

The non-linear optical article constituted of a derivative of benzalacetophenone, according to this invention, has extremely high non-linear optical effect and has a percent transmission of 100% light rays having wave lengths of not less than 400 nm, and thus it may be used for various optical processing of the light rays as an optical element or tool which is excellent in transparency.

EXAMPLES OF THE INVENTION

The present invention will now be described more specifically with reference to some Examples and Comparative Examples. However, it is noted that the following Examples are intended to be only illustrative and not limiting, and the invention should be limited only by the appended claims.

EXAMPLE 1

Into a reaction vessel provided with a stirrer, charged was 60 g of a 10% aqueous sodium hydroxide solution, a solution containing 16.2 g of paraaminoacetophenone dissolved in 100 g of ethanol was added dropwise, while agitating at 0° C. over a period of 15 minutes. After the completion of dropwise addition, a solution containing 16.3 g of paramethoxybenzaldehyde dissolved in 50 g of ethanol was added dropwise at the same temperature over a period of 15 minutes. After the completion of dropwise addition of the paramethoxybenzaldehyde solution, the contents of the reaction vessel were raised to 25° C., and then allowed to react for an additional 6 hours.

After the completion of the reaction, the separated precipitate was filtered and dried at room temperature for 24 hours under a reduced pressure, whereby 29.5 g of a raw product of 3-(4-methoxyphenyl)-1-(4-aminophenyl)-2-propene-1-one was obtained. The yield was 97%.

The raw product was recrystallized from ethanol to obtain 20.7 g of a refined product. The yield at this stage was 82%.

The refined product was analysed by high speed liquid chromatography (using a chromatogram analyser #LC-6A produced by Shimadzu Seisakusho Co. Ltd.) to find that the purity was 99.9%. The melting point of the refined product was 150.5° C.

The second harmonic generation (SHG) was measured in the following manner. A granulated sample having a granule diameter of 50 to 150 microns was sandwiched between slide glass plates, the sample being exposed to a pulse irradiation of an Nd-YAG laser beam (1064 nm) provided with Q-switch for 15 n sec., and second harmonic waves emitted from the sample were detected. Similarly granulated urea was used as the control sample; the relative SHG intensity of the sample was calculated while the SHG intensity of the urea sample was taken as the standard value of 1. This method has been well known to a person having ordinary skill in the art, and is disclosed, for example, in Journal of Applied Physics, Vol. 36, No. 8, pages 3798 to 3813 (1968) which is hereby incorporated herein by reference.

The results of the determination of the SHG intensity of the sample of this Example revealed that the SHG intensity thereof was 30.7 times as high as that generated from urea.

EXAMPLE 2

Into a reaction vessel provided with a stirrer, charged was a solution containing 16.3 g of paramethoxybenzaldehyde and 23.9 g of parabromoacetophenone dissolved in 120 g of dioxane, 18 g of boron trifluoride etherate was added dropwise at 0° C. over a period of 20 minutes under agitation. After the completion of dropwise addition, the contents of the reaction vessel were reacted at 25° C. for 7 hours. After the completion of the reaction, the reaction solution was cooled sufficiently with ice, followed by gradual hydrolysis by the addition of water, and then extracted three times with diethyl ether. The ether phase was rinsed with water and then dried to obtain 37.3 g of a raw product of 3-(4-methoxyphenyl)-1-(4-bromophenyl)-2-propene-1-one. The yield of the raw product was 98%.

The raw product was recrystallized from ethanol to obtain 32.2 g of a refined prodcut. The yield of the refined product was 85%. The refined product was analysed by high speed liquid chromatography to find that the purity thereof was 99.7%. The melting point of the refined product was 148.5° C.

Generally following the procedure as described in Example 1, the SHG intensity of the refined product was determined to find that the SHG intensity thereof was 13.3 times as high as that of urea.

EXAMPLE 3

Into a reaction vessel provided with a stirrer, charged was 60 g of a 10% aqueous solution of sodium hydroxide, to which a solution containing 18 g of paramethoxyacetophenone dissolved in 50 g of ethanol was added dropwise at 0° C. over 10 minutes under stirring. After the completion of dropwise addition, a solution containing 17.9 g of paradimethylaminobenzaldehyde dissolved in 100 g of ethanol was added dropwise at the same temperature over 15 minutes, after which the reaction temperature was raised to 25° C. and the reaction was continued for 5 hours.

After the completion of the reaction, the separated precipitate was filtered and then dried at room temperature for 24 hours under a reduced pressure to obtain 32.7 g of a raw product of 3-(4-dimethylaminophenyl)-1-(4-methoxyphenyl)-2-propene-1-one. The yield of the raw product was 97%.

The raw product was recrystallized from ethanol to obtain 30.5 g of a refined product. The yield of the refined product was 85%.

The refined product was analysed by liquid chromatography to find that the purity was 99.8%. The melting point of the refined product was 131° C.

The SHG intensity of the sample of this Example was determined, similarly as in Example 1, to find that the SHG intensity thereof was 20.0 times as high as that of urea.

EXAMPLE 4

Into a reaction vessel provided with a stirrer, charged was a solution containing 22.2 g of parabromobenzaldehyde and 18 g of paramethoxyacetophenone dissolved in 100 g of dioxane, to which there was added dropwise 17 g of boron trifluoride etherate at 0° C. over a period of 20 minutes under stirring.

After the completion of dropwise addition, the contents of the vessel were reacted at 25° C. for 8 hours. After the completion of the reaction, the reaction solution was cooled with ice sufficiently, followed by slow or gentle hydrolysis by the addition of 100 g of water, and subjected three times to extraction with diethyl ether. The ether phase was rinsed with water and then dried to obtain 21.6 g of a raw product of 3-(4-bromophenyl)-1-(4-methoxyphenyl)-2-propene-1-one. The yield of the raw product was 98%.

The raw product was recrystallized from ethanol to obtain 18.3 g of a refined product. The yield of the refined product was 83%. The refined product was analysed by high speed liquid chromatography to find that the purity thereof was 99.8%. The melting point of the same was 96° C.

The SHG intensity of the sample of this Example was determined, similarly as in Example 1, to find that the SHG intensity thereof was 26.7 times as high as that of urea.

EXAMPLE 5

Into a reaction vessel provided with a stirrer, charged was 70 g of an 8% aqueous solution of sodium hydroxide, to which there was added dropwise a solution containing 18 g of paramethoxyacetophenone dissolved in 50 g of ethanol at 3° C. over a period of 10 minutes under stirring. After the completion of dropwise addition, another solution containing 18 g of paraethoxybenzaldehyde dissolved in 50 g of ethanol was added dropwise over a period of 10 minutes at the same temperature. After the completion of dropwise addition, the reaction temperature was raised to 25° C., and then the reaction was continued for 6 hours.

After the completion of the reaction, the separated precipitate was filtered and dried at room temperature for 24 hours under a reduced pressure to obtain 32.5 g of a raw product of 3-(4-ethoxyphenyl)-1-(4-methoxyphenyl)-2-propene-1-one. The yield of the raw product was 96%.

The raw product was recrystallized from ethanol to obtain 28.8 g of a refined product. The yield of the refined product was 85%.

The refined dproduct was analysed by liquid chromatography to find that the purity thereof was 99.9%. The melting point thereof was 111° C.

The SHG intensity of the sample of this Example was determined, similarly as in Example 1, to find that the SHG intensity thereof was 20.0 times as high as that of urea.

EXAMPLE 6

Into a reaction vessel provided with a stirrer, charged was 50 g of a 10% aqueous solution of sodium hydroxide, to which there was added dropwise a solution containing 14.4 g of acetophenone dissolved in 40 g of ethanol at 0° C. over a period of 10 minutes while stirring the contents of the reaction vessel. After the completion of dropwise addition, a solution containing 22.2 g of parabromobenzaldehyde dissolved in 100 g of ethanol was added dropwise at the same temperature over a period of 15 minutes. After the completion of dropwise addition, the reaction temperature was raised to 25° C., and the reaction was continued for 5 hours.

After the completion of the reaction, the separated precipitate was filtered and then dried at room temperature for 24 hours under a reduced pressure to obtain 33.8 g of a raw product of 3-(4-bromophenyl)-1-phenyl-2-propene-1-one. The yield of the raw product was 98%.

The raw product was recrystallized from ethanol to obtain 30.3 g of a refined product. The yield of the refined product was 88%.

The refined product was analysed by high speed liquid chromatography to find that the purity thereof was 99.9%. The melting point thereof was 126° C.

The SHG intensity of the sample of this Example was determined, similarly as in Example 1, to find that the SHG intensity thereof was 13.3 times as high as that of urea.

EXAMPLE 7

The procedure as described in Example 2 was repeated except that 14.4 g of acetophenone was used in place of parabromoacetophenone as used in Example 2, whereby 27 g of a raw product of 3-(4-paramethoxyphenyl)-1-phenyl-2-propene-1-one was obtained. The yield was 88%.

The analysis of a refined product by high speed liquid chromatography revealed that the purity thereof was 99.9%. The melting point of the same was 76.8° C.

The SHG intensity of the sample of this Example was determined, similarly as in Example 1, to find that the SHG intensity thereof was 6.7 times as high as that of urea.

COMPARATIVE EXAMPLES 1 TO 3

SHG intensities of the samples of the derivatives of benzalacetophenone having nitro- and methyl-groups, which are described in the article entitled "Organic Materials for Optical Sound Harmonic Generation" published in the Collection of Prearranged Report for the Symposium of American Chemical Society held in 1983, were determined in the manner similar to that described in Example 1. The results are set forth in Table 1 together with the results of Examples 1 to 7.

TABLE 1

| | Structural Formula | Relative Intensity of SHG |
|---|---|---|
| Example 1 | $CH_3O-\text{C}_6H_4-CH=CH-CO-\text{C}_6H_4-NH_2$ | 30.7 |
| Example 2 | $CH_3O-\text{C}_6H_4-CH=CH-CO-\text{C}_6H_4-Br$ | 13.3 |
| Example 3 | $(CH_3)_2N-\text{C}_6H_4-CH=CH-CO-\text{C}_6H_4-OCH_3$ | 20.0 |
| Example 4 | $Br-\text{C}_6H_4-CH=CH-CO-\text{C}_6H_4-OCH_3$ | 26.7 |
| Example 5 | $C_2H_5O-\text{C}_6H_4-CH=CH-CO-\text{C}_6H_4-OCH_3$ | 20.0 |
| Example 6 | $Br-\text{C}_6H_4-CH=CH-CO-\text{C}_6H_5$ | 13.3 |
| Example 7 | $CH_3O-\text{C}_6H_4-CH=CH-CO-\text{C}_6H_5$ | 6.7 |
| Comparative Example 1 | $CH_3O-\text{C}_6H_4-CH=CH-CO-\text{C}_6H_4-NO_2$ | 5.0 |
| Comparative Example 2 | 2,6-Cl$_2$-$\text{C}_6H_3$-CH=CH-CO-$\text{C}_6H_4$-NO$_2$ | 4.0 |

TABLE 1-continued

| Structural Formula | Relative Intensity of SHG |
| --- | --- |
| Comparative Example 3 CH₃—⌬—CH=CH—C(=O)—⌬—CH₃ | 1.0 |

Although the present invention has been described with reference to specific examples, it should be understood that various modifications and variations can be easily made by those skilled in the art without departing from the spirit of the invention. Accordingly, the foregoing disclosure should be interpreted as illustrative only and not to be interpreted in a limiting sense. The present invention is limited only by the scope of the following claims.

What is claimed is:

1. In a non-linear optical device in which an organic compound is disposed in a light beam, the improvement in which the organic compound is a derivative of benzalacetophenone selected from the group represented by the following general formula

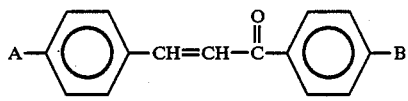

wherein A is $CH_3O$— in case of B being —$NH_2$, —Br or —H; A is $(CH_3)_2N$—, Br— or $C_2H_5O$— in case of B being —$OCH_3$; and A is Br— in case of B being —H.

2. The non-linear optical device according to claim 1, wherein said derivative of benzalacetophenone has a percent transmission of 100% to the visible light rays having the wavelengths of not less than 400 nm.

* * * * *